United States Patent [19]
Masuda et al.

[11] Patent Number: 5,417,836
[45] Date of Patent: May 23, 1995

[54] ION-SELECTIVE ELECTRODE

[75] Inventors: Chie Masuda; Jun-ichi Tokumoto, both of Aichi, Japan

[73] Assignee: NGK Spark Plug Co., Ltd., Aichi, Japan

[21] Appl. No.: 284,980

[22] Filed: Aug. 4, 1994

[30] Foreign Application Priority Data

Aug. 5, 1993 [JP] Japan .................. 5-212093

[51] Int. Cl.6 .............................. G01N 27/26
[52] U.S. Cl. .................. 204/419; 204/416; 204/435
[58] Field of Search ............... 204/419, 418, 416, 435

[56] References Cited

U.S. PATENT DOCUMENTS

| | | | |
|---|---|---|---|
| 3,607,710 | 9/1971 | Farren et al. | 204/416 |
| 4,214,968 | 7/1980 | Battaglia et al. | 204/419 |
| 4,454,007 | 6/1984 | Pace | 204/416 |
| 4,597,848 | 7/1986 | Oka et al. | 204/418 |
| 4,686,012 | 8/1987 | Engell et al. | 204/419 |
| 5,120,422 | 6/1992 | Liu et al. | 204/416 |
| 5,192,404 | 3/1993 | Fray et al. | 204/419 |
| 5,308,468 | 5/1994 | Katoh et al. | 204/419 |

FOREIGN PATENT DOCUMENTS 56-5687  6/1981  Japan .
5-80019  3/1993  Japan .

OTHER PUBLICATIONS

Fabry et al., "Internal Ionic Bride for Ion Solid State Sensors", Proc. of the 2nd Int. Meeting on Chemical Sensors, Bordeaux 1986, 5-02, pp. 473-476. no month available.

Fabry et al., "Nasicon, An Ionic Conductor for Solid-State, Na+-Selective Electrode", Sensors and Actuators, 15 (1988) 33-49. no month available.

H. Y-P. Hong, "Crystal Structures and Crystal Chemistry in the System $Na_{1+x}Zr_2Si_xP_{3-x}O_{12}$", Mat. Res. Bull. vol. 11, Pergamon Press, Inc. 1976, pp. 173-182. no month availiable.

*Primary Examiner*—Kathryn Gorgos
*Assistant Examiner*—Bruce F. Bell
*Attorney, Agent, or Firm*—Fish & Richardson

[57] ABSTRACT

An ion-selective electrode comprises, in order of enumerating from the measured-ion contact side: a solid electrolyte as an ion-sensitive membrane; an ionic bridge layer; and, an internal electrode. The bridge layer is prepared by mixing a salt mixture with an electrically conductive resin composition at a ratio of 1:2 to 3:1 in weight, determined after heat treatment. The salt mixture is prepared by mixing silver halide with sodium phosphate at a ratio of from 9:1 to 3:7 in weight. The electrode is very small in voltage fluctuation detected among products; easily downsized to be capable of measuring a very small amount of a sample solution; and useful in measuring activity of ion species such as Na-ion.

21 Claims, 7 Drawing Sheets

ION-SELECTIVE ELECTRODE

FIELD OF THE INVENTION

The present invention relates to an ion-selective electrode used in medical measurements (i.e., clinical inspections), water examinations, and process controls in food industries and chemical industries.

BACKGROUND

In the case of detecting ions in a sample solution, there is used an ion-selective electrode method in which an ion-selective electrode is used. The ion-selective electrode is an electrode for detecting a potential difference corresponding to ion activities (i.e., thermodynamically compensated concentration) of anions and cations in a solution, and is provided with an ion sensitive (or responsive) member (membrane) which is sensitive to a specific ionic species.

Most ion-selective electrodes of conventional types require internal solutions, and, therefore are large in size and require ample quantities of sample solutions to be measured. In contrast with this, there is another type of ion-selective electrode, i.e., an all-solid-types which employ solid membranes such as solid electrolytes in their ion sensing portions (i.e., sensitive membranes) and which do not require any internal solution. In the latter types, there are two methods for detecting electric potentials: in the first one, a lead wire is directly connected with the responsive membrane to read the electric potentials; and, in the second one, the lead wire is connected with the sensitive membrane through a solid internal electrolyte layer employed in place of the internal solution to read the electric potentials, the layer being called an ionic bridge. However, the first one is poor in response time and stability in operation, which makes it difficult to obtain reliable data.

P. Fabry et al. have disclosed, in their paper "Internal Ionic Bridge for Ion Solid State Sensors, proc. of 2nd Int. Meeting on Chemical Sensors, Bordear 1986, 5-02, pp. 473-476", an ion-selective electrode in which: the NASICON, which is a solid electrolyte, is used as a solid state membrane; and, polyethylene oxide (PEO) doped with Na-ion and M-(i.e., Cu, Ag-)ion is used as an ionic bridge. As a result, the following electrochemical equation chain is clarified.

P. Fabry et al. have further disclosed, in their paper "NASICON, an ionic conductor for solid-state $Na^+$-selective electrode, Sensor and Actuators 15 (1988), pp. 33-49", a Na-ion sensor cell assembly, which is constructed of: a NASICON pellet, a lead wire made of Ag or Ag-Cd alloy, and a molten-salt type ionic bridge interposed therebetween, the ionic bridge being bonded to layers of opposite sides disposed thereto through melting/cooling operations. The ionic bridge forms an ion-conductive intermediate layer through which ions are transmitted from a solid state membrane to an internal metallic conductor (which forms a lead electrode or internal electrode). Ionic conductivities of Na- and Ag- ions are realized in the ionic bridges of AgCl-NaCl type or of AgI-NaI type, which show maximum deviations of 20 mV or 40 mV each.

The applicant of the present invention has disclosed, in Japanese Patent kokai Publication No. Hei 5-80019 (1993), an ion-selective electrode in which an ionic bridge layer is prepared by having an electrically conductive resin composition doped with at least one of salt, solid solution and solid electrolyte.

PROBLEMS TO BE SOLVED BY THE INVENTION

According to eager investigation of the inventors, the following points have been revealed as problems.

In order to obtain stable electric potentials, the ionic bridge layer is prepared by using the polyethylene oxide (PEO) polymer composition doped with salts (iodides) of Na and M, or by using salts or molten ones thereof (solid solutions). However, the thus prepared ionic bridge layer shows poor adhesions to both the solid electrolyte sensitive membrane and the lead electrode, and is also poor in mechanical strength, which results in fluctuations in output voltages among products.

The above-mentioned problems have been considerably solved in the Japanese Patent kokai Publication No. Hei 5-80019 (1993), but not sufficiently solved therein.

OBJECT

Consequently, it is an object of the present invention to provide a novel ion-selective electrode, through which the above problems are solved to make it possible to control fluctuations in outputs between products so as to obtain stable outputs.

Further, it is another or second object of the present invention to provide an ion-selective electrode having an extended service life.

It is a further or third object of the present invention to provide an ion-selective electrode which is low in cost and easily available.

Still further objects will become apparent in the entire disclosure.

SUMMARY OF THE DISCLOSURE

Consequently, the above objects of the present invention are accomplished by providing the following means: namely, In an ion-selective electrode comprising, in order of enumerating from the measured-ion contact side: a solid electrolyte serving as an ion-sensitive membrane, an ionic bridge layer, and an internal electrode, the improvement wherein:

the ionic bridge layer is prepared by mixing a salt mixture with an electrically conductive resin composition at a salt mixture:resin ratio of 1:2 to 3:1 in weight provided that the weight of the electrically conductive resin composition is determined after completion of heat treatment thereof, the salt mixture being prepared by mixing a silver halide with a sodium phosphate at a former:latter ratio of 9:1 to 3:7 in weight.

The following basic action and/or function are exhibited according to the present invention.

Due to the fluidity of the electrically conductive resin composition, it is possible to apply the ionic bridge layer onto the solid electrolyte sensitive membrane. As a result, it is possible to apply the ionic bridge layer onto the solid electrolyte sensitive membrane in an easy manner even when the surface area of the membrane is very small, which permits the electrode to be downsized. Further, since the electrically conductive resin composition may be reactively matured (cured) through heating operations to permit its volatile components to dissipate, it is possible to improve the ionic bridge layer in adhesion to the solid electrolyte sensitive membrane.

Further, as already described above, when the ionic bridge layer is constructed only of the PEO polymer doped with the salts, the detected voltages among the products widely fluctuate. However, in the present invention, the electrically conductive resin composition is used and doped with salts such as sodium phosphate and silver halide, which easily realizes reversible equilibrium states between the conductive ion species of the solid electrolyte sensitive membrane and the above salts mixed into the ionic bridge layer. Further, it is also possible to reduce the fluctuations of the detected voltages among the products by the provision of the above two kinds of the salts, which also improves the ion-selective electrode in durability.

The following fact has been found by the inventors of the present invention: the fluctuations in detected voltages between the products are smaller with a mixture in which both the silver halide and the sodium phosphate are mixed as salts in the electrically conductive resin composition than with a mixture in which only the silver halide is mixed as a salt in the electrically conductive resin composition.

Heretofore, in case where the sodium salt is mixed as a salt in the electrically conductive resin composition, sodium halide (for example, as disclosed in the Japanese Patent kokai Publication No. Hei 5-80019) has been employed. However, in the present invention, sodium phosphate is employed, which makes it possible to realize an ion-selective electrode with minimum fluctuation in the detected voltage among the products. The reason why the ion-selective electrode is minimized in fluctuation of the detected voltage seems to be that the affinity of sodium phosphate for the solid electrolyte sensitive membrane is larger than the affinity of the sodium halide for the solid electrolyte sensitive membrane in ion exchanging operation.

On the other hand, in the addition of sodium polyphosphate, no improvement is recognized in fluctuation of the detected voltage.

Incidentally, sodium phosphate is lower in cost than the solid electrolyte, and, therefore easily available. Further, in the present invention, silver halides and sodium phosphate are sufficiently mixed/kneaded, and then mixed in the electrically conductive resin composition, which is simple in operation to eliminate the need for preparing the solid solutions.

The following meritorious effects are observed according to the present invention.

The ion-selective electrode of the present invention as set forth in claim 1 is of an all-solid-state type, and is provided with the ionic bridge layer which is prepared by mixing the salt mixture with the electrically conductive resin composition, the salt mixture comprising silver halide and sodium phosphate. Consequently, the ion-selective electrode of the present invention has following excellent meritorious effects:

(1) the fluctuations of the detected voltages among the products of the ion-selective electrode of the present invention are very small;

(2) the ion-selective electrode of the present invention may be easily downsized to permit the electrode to perform potentiometric measurement on a very small amount of the sample solution;

(3) the ion-selective electrode of the present invention may be formed into any desired shape such as plate-like shapes, sleeve-like shapes, needle-like shapes and the like, which makes it possible to select an optimum one of the electrodes suitable for each of measuring fields and objectives; and (4) the ion-selective electrode of the present invention is easy in maintenance.

Further, according to the present invention, it is possible to improve the ion-selective electrode in durability and to produce the same in a low cost.

DESCRIPTION OF THE REFERENCE SYMBOLS

A: ion-selective electrode
1: ion-selective electrode portion
1a: internal electrode
1b: ionic bridge layer
1c: ion-responsive membrane

DETAILED DESCRIPTION OF PREFERRED EMBODIMENTS

The internal electrode is a portion for taking out electric potentials, and made of metal selected to be excellent in electrical conductivity, among which, copper is most preferred. Where the internal electrode is made of copper thus selected, it is possible to provide an ion-selective electrode with minimum fluctuation in detected voltages among the products of the ion-selective electrode. Further, copper is advantageous in cost in comparison with noble metals such as silver and the like, and, therefore permits the ion-selective electrode to be manufactured in a low cost.

The electrically conductive resin composition is an adhesive resin which is excellent in adhesion to both the solid electrolyte and the lead electrode metal and doped with powdery electrically conductive materials such as metals and carbon. Preferable ones of such resin compositions are, for example, thermoset resins such as epoxy reins and phenolic resins, provided that these thermoset resins: are doped with the electrically conductive materials; are pastes good in flow properties in their initial stage; and, are reactively matured (cured) through heat treatment in which their volatile components are dissipated.

The salt mixture composed of the silver halide and the sodium phosphate is mixed with the electrically conductive resin composition at a salt mixture: resin ratio of from at least 1:2 to 3:1 in weight, preferable a ratio of 1:1 in weight. In this case, the weight of the electrically conductive resin composition is determined after completion of the heat treatment thereof. When the amount of the salts being mixed is smaller than the amount specified in the above, the resultant ion-selective electrode is poor in response and the fluctuation of the detected voltages among the products cannot be sufficiently suppressed. On the other hand, where the amount of the salts being mixed is larger than the amount specified in the above, the above-mentioned pastes tend to be poor in flow properties, which makes it difficult to apply the pastes to the internal electrode to impair its adhesion properties to the sensitive membrane.

The amount of the powdery electrically conductive materials contained in the electrically conductive resin composition is within a range of from 10 to 60 wt %, preferably from 20 to 50 wt %. Carbon powder (or graphite powder) is one of the most preferred materials to be contained, and preferably has a grain size, in the secondary order, of about 0.1 micrometer (the secondary grain may be composed of agglomerated primary-order carbon particles the number of which is several (6 or 7) and the primary grain size of which is ordinarily within a range of from 20 to 30 nanometers). Resins each used as the electrically conductive resin composition may be selected from those resins, such as unsaturated polyester resins, acrylic resins, polyurethane resins and like resins, which are good in flowability in their initial stage and may be reactively matured (or cured) to have large adhesive strengths. Incidentally, it is natural that the thus selected resins each preferably have water resistance.

The salt mixture mixed in the electrically conductive resin composition is composed of silver halide and sodium phosphate. The silver halide embraces silver chloride, silver bromide, silver iodide and the like, most preferably, silver chloride. On the other hand, the sodium phosphate embraces sodium dihydrogen phosphate, disodium hydrogen phosphate, trisodium phosphate, mixtures thereof, and/or hydrates thereof, most preferably trisodium phosphate or 12-hydrate thereof. The ratio of the silver halide to the sodium phosphate in the salt mixture is: within a range of 9:1 to 3:7, preferably 9:1 to 7:3; and, most preferably 8:2 (i.e., 4:1), in weight.

If the amount of the sodium phosphate thus mixed is less than that specified in the above, it is not possible for such addition of the sodium phosphate to have a sufficient suppressing effect on the fluctuations of the detected voltages among the products. On the other hand, if the amount of the sodium phosphate thus mixed is more than that specified in the above, the effect of the sodium phosphate on the fluctuations of the detected voltages among the electrode products disappears. Particularly, in case where a large amount of the hydrate is added, the ionic bridge layer (or member) is impaired in adhesion to the remaining members: the solid electrolyte sensitive membrane and the internal electrode, due to evaporation of the hydrates during the heat treatment, which causes peeling off at the interface between these members.

Incidentally, it is preferred that the above salts are in a powdery state having a mean grain size of 50 micrometers or less, more preferably 10 micrometers or less.

In general, the solid electrolyte sensitive membrane has an ionic sensibility inherent in its conductive ion species. In the present invention the solid electrolyte sensitive membranes can be used as long as they satisfy the following requirements: form a dense film; and, are stable even in the sample solution being measured. Particularly good are Na-ion conductive ceramics, for example such as Na-$\beta$-alumina or Na-$\beta''$-alumina, NASICON and like ceramics. Incidentally, each of the solid electrolyte ceramics used in the present invention has a relative density of at least 95%, preferably 99% or more, and has a mean grain size of not more than 10 micrometers, preferably not more than 5 micrometers. In the present invention, by changing the solid electrolyte sensitive membrane material, it is possible for the ion-selective electrode of the present invention to measure the activity of the other ionic species in addition to the Na-ion.

EXAMPLES

Figure 1:
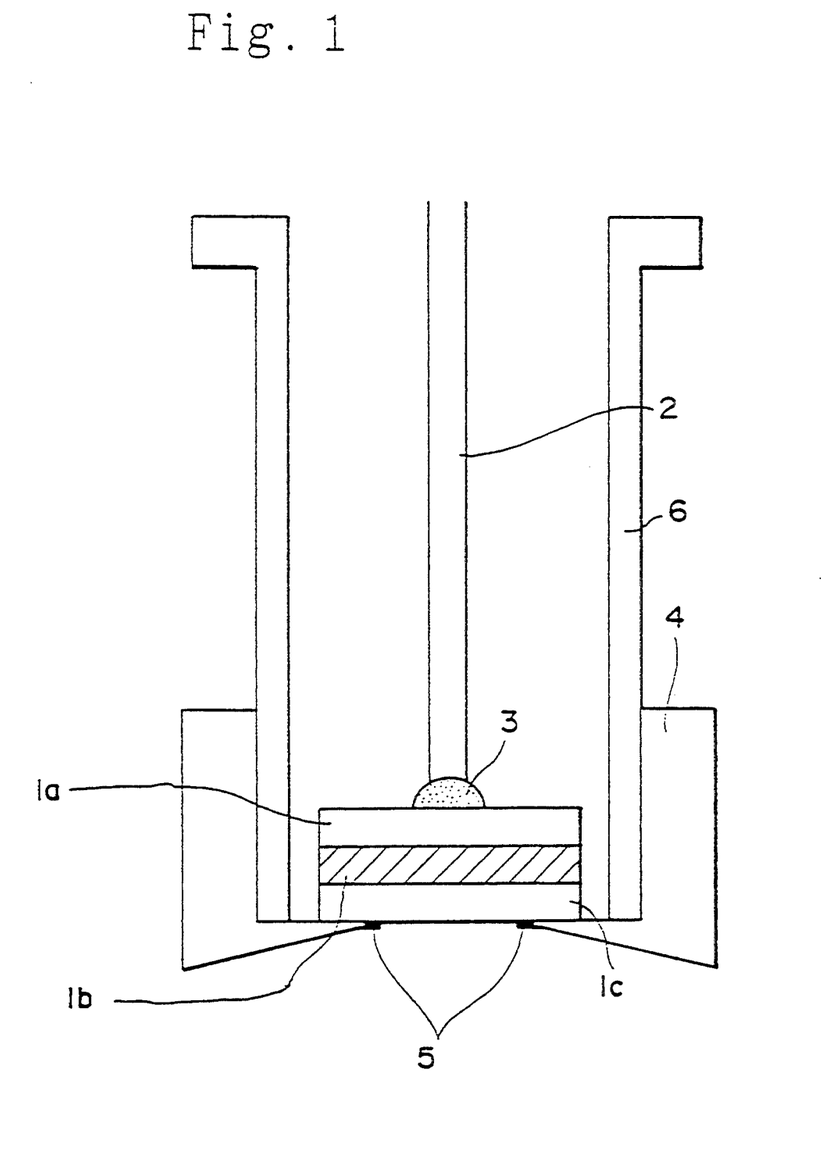
FIG. 1: A diagram (cross-section) illustrating an ion-selective electrode of one of the embodiments of the present invention.

Example 1 (See FIG. 1)

(1) A disc having dimensions: 7 (diameter)×0.5 (thickness) mm made of NASICON sintered material (which is prepared by molding a powdery composition $Na_3Zr_2Si_2PO_{12}$ and sintering the resultant molded mass) is prepared . . . 1c (2) Silver chloride and the sodium dihydrogen phosphate dihydrate are sufficiently mixed with each other at a former:latter ratio of 4:1 in weight to prepare a powder mixture.

(3) A carbon paste is prepared by admixing carbon to the phenolic resin to prepare an electrically conductive resin composition (which is, for example, the product "DOTITE" (trade name) available from Fujikura Kasei K.K. The thus prepared carbon paste is then mixed with the powder mixture (which is specified in the above step (2)) at a ratio of 1:1 in weight.

(4) A lead wire 2 is previously connected with a copper electrode (i.e., internal electrode) 1a through a solder 3 by soldering. The paste prepared in the above step (3) is applied to the internal electrode 1a to form a paste film, to which the NASICON plate 1c prepared in the above step (1) is superposed to permit the paste film to form a laminated member 1b.

(5) The laminated member 1b prepared in the above step (4) is then heat-treated at a temperature of 150° C. for an hour to permit the paste prepared in the above step (3) to cure, so that the laminated member (i.e., ionic bridge layer) 1b is bonded to the copper plate 1a. The paste film was about 1 mm thick after the heat treatment.

(6) The NASICON plate 1c is sealed with an epoxy resin 5 to an ABS-resin cap 4 to be hermetically bonded to the cap 4 so that the plate 1c has a 25% of its outermost surface area be exposed (to a sample-solution side).

(7) An electrode supporting sleeve 6, which is made of the ABS resin, is fixedly mounted on the cap 4 specified in the above step (6).

As described above, the sodium-ion-selective electrode was prepared so as to have a construction shown in FIG. 1, in which: the ionic bridge layer 1b is prepared by admixing the salt mixture (which contains silver halide and sodium phosphate) to the electrically conductive resin composition; and, the NASICON plate 1c is the solid electrolyte ceramic forming an ion-sensitive membrane 1c.

Example 2

Silver chloride and disodium hydrogen phosphate were mixed with each other at a former:latter ratio of 4:1 in weight to prepare a mixture. This mixture, in place of the mixture specified in the above step (2) of Example 1, was mixed with the carbon paste, as prepared by the step (3) of EXAMPLE 1 to prepare a sodium-ion-selective electrode.

Example 3

Silver chloride and trisodium phosphate 12-$H_2O$ were mixed with each other at a former:latter ratio of 4:1 in weight to prepare a mixture. This mixture, in place of the mixture specified in the above step (2) of Example 1, was mixed with the carbon paste to prepare a sodium-ion-selective electrode.

Example 4

Silver bromide and trisodium phosphate 12-$H_2O$ were mixed with each other at a former:latter ratio of 4:1 in weight to prepare a mixture. This mixture, in place of the mixture specified in the above step (2) of Example 1, was mixed with the carbon paste to prepare a sodium-ion-selective electrode.

Example 5

Silver iodide and trisodium phosphate 12-$H_2O$ were mixed with each other at a former:latter ratio of 4:1 in weight to prepare a mixture. This mixture, in place of the mixture specified in the above step (2) of Example 1, was mixed with the carbon paste to prepare a sodium-ion-selective electrode.

Example 6

Silver chloride and disodium hydrogen phosphate were mixed with each other at a former:latter ratio of 3:2 in weight to prepare a mixture. This mixture, in place of the mixture specified in the above step (2) of Example 1, was mixed with the carbon paste to prepare a sodium-ion-selective electrode.

Example 7

Silver chloride and disodium hydrogen phosphate were mixed with each other at a former:latter ratio of 2:3 in weight to prepare a mixture. This mixture, in place of the mixture specified in the above step (2) of Example 1, was mixed with the carbon paste to prepare a sodium-ion-selective electrode.

Example 8

A sodium-ion-selective electrode having the same construction as that of Example 3 was prepared, provided that the internal electrode 1a of Example 8 was made of silver.

Comparative Example 1

A sodium-ion-selective electrode provided with an ionic bridge layer made of the carbon paste only was prepared in the same manner as that of Example 1, provided that the step (2) of Example 1 was eliminated in Comparative example 1.

Comparative Example 2

The carbon paste and the powder mixture specified in the above step (2) of Example 1 were sufficiently mixed with each other at a former:latter ratio of 3:1 in weight to prepare a mixture. This mixture, in place of the mixture specified in the above step (3) in Example 3, was used to prepare a paste forming the ionic bridge layer (provided that a carbon paste having the same composition as that of the carbon paste specified in Example 3 was used), so that a sodium-ion-selective electrode was prepared.

Comparative Example 3

Silver chloride and disodium hydrogen phosphate were sufficiently mixed with each other at a former:latter ratio of 1:4 in weight to prepare a mixture. This mixture, in place of the mixture specified in the above step (2) in Example 1, was mixed with the carbon paste to prepare a sodium-ion-selective electrode.

Figure 2:
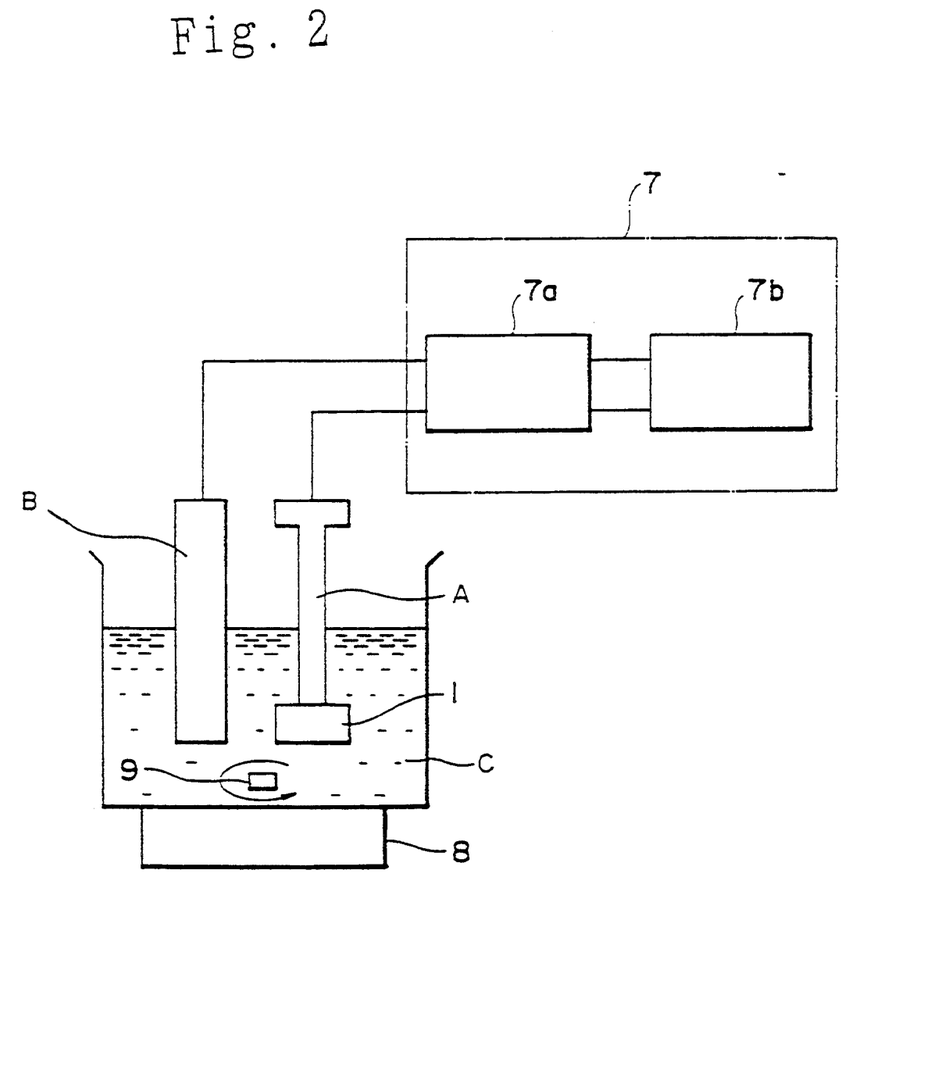
FIG. 2: A schematic block diagram illustrating one embodiment of the ion-concentration measuring method using the ion-selective electrode of the present invention.
Figure 3:
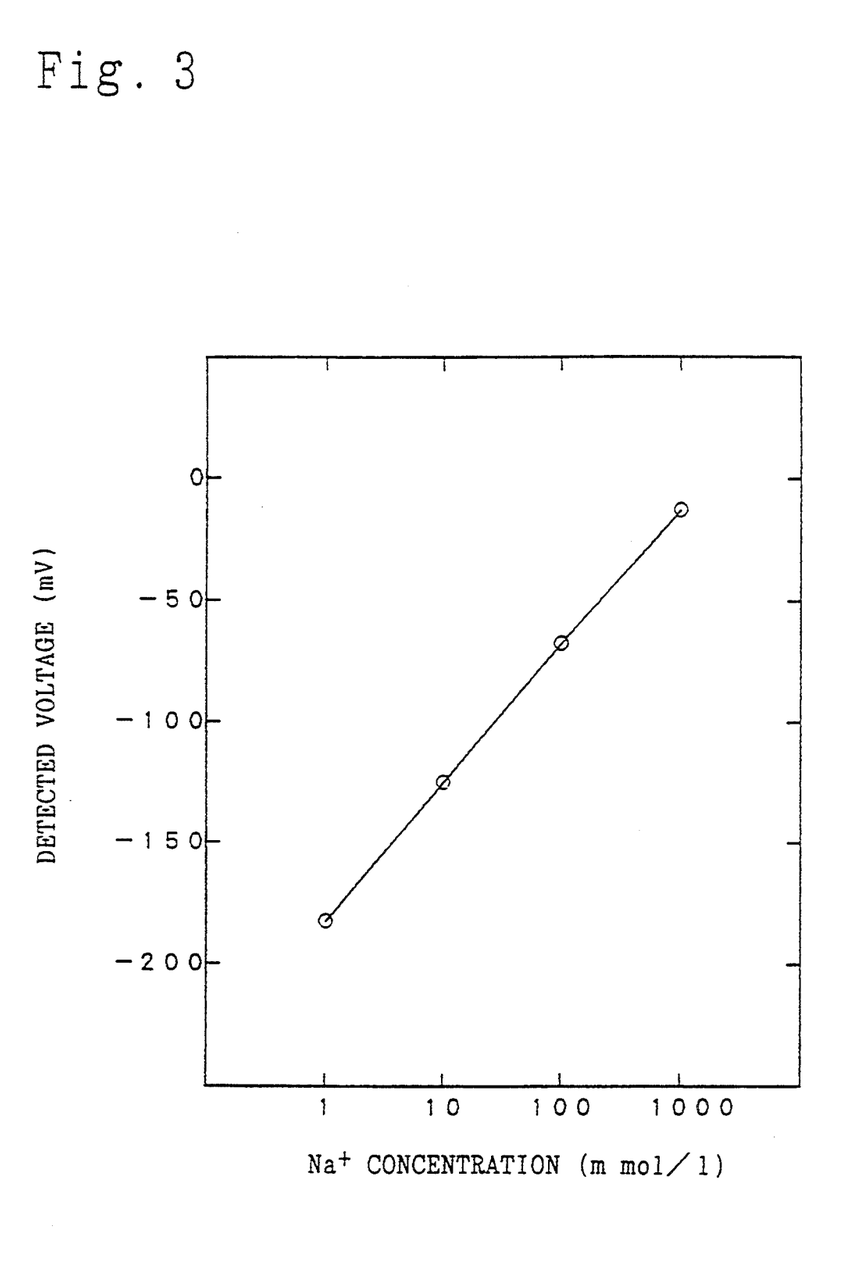
FIG. 3: A graph illustrating the variation of electric potential based on the ion concentration in a measuring test using an ion-selective electrode formed of an ionic bridge layer of Example 1.
Figure 4:
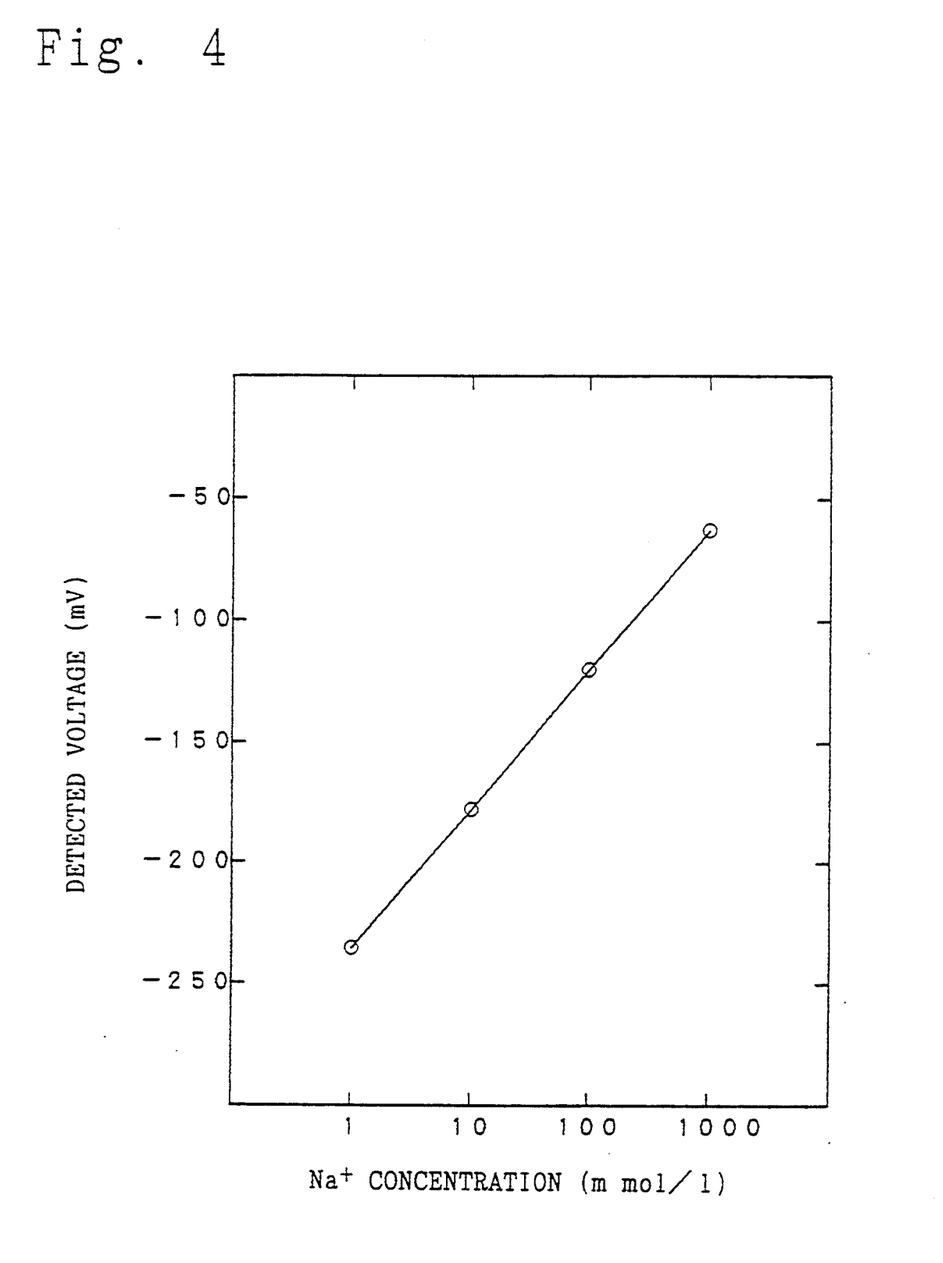
FIG. 4: A graph illustrating the variation in electric potential based on the ion concentration in a measuring test using an ion-selective electrode formed of an ionic bridge layer of Example 2.
Figure 5:
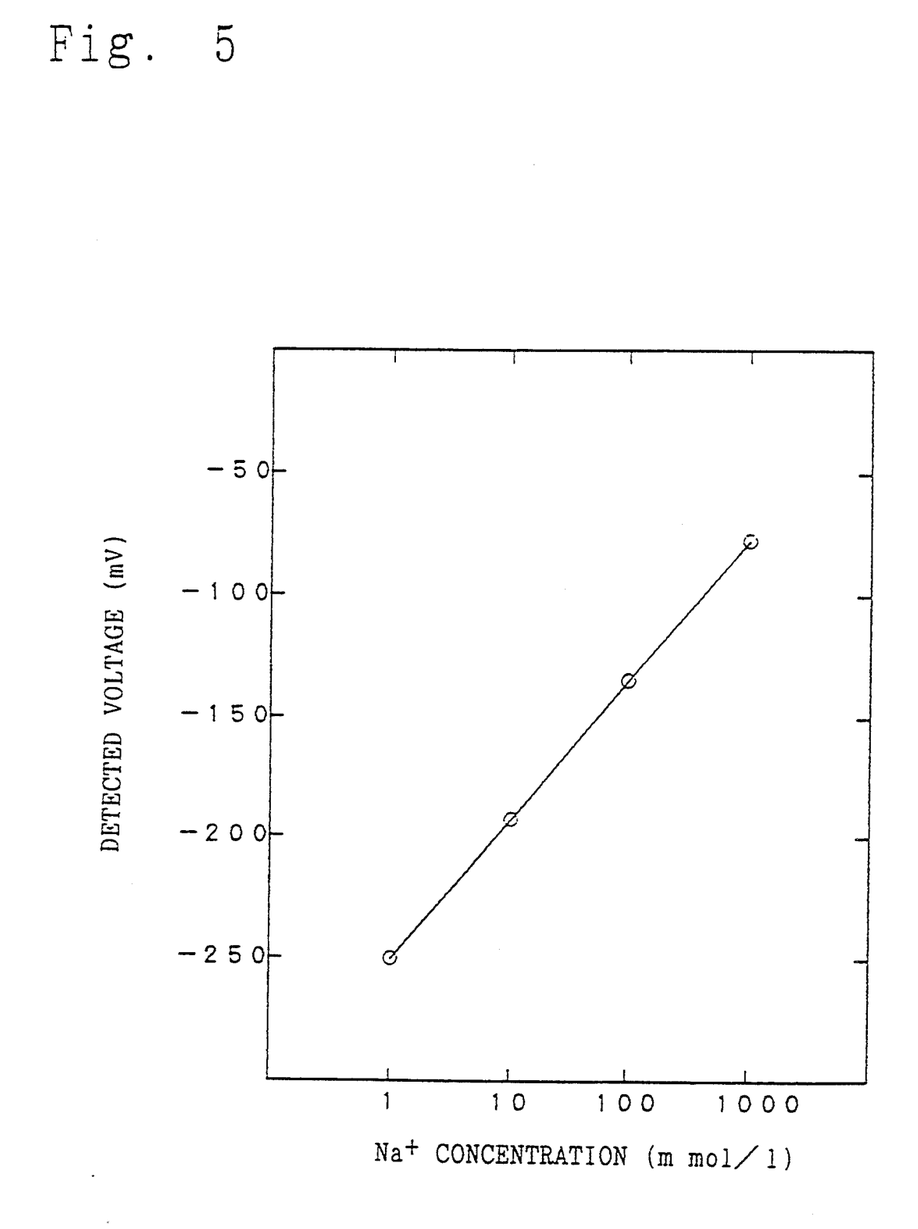
FIG. 5: A graph illustrating the variation in electric potential based on the ion concentration in a measuring test using an ion-selective electrode formed of an ionic bridge layer of Example 3.
Figure 6:
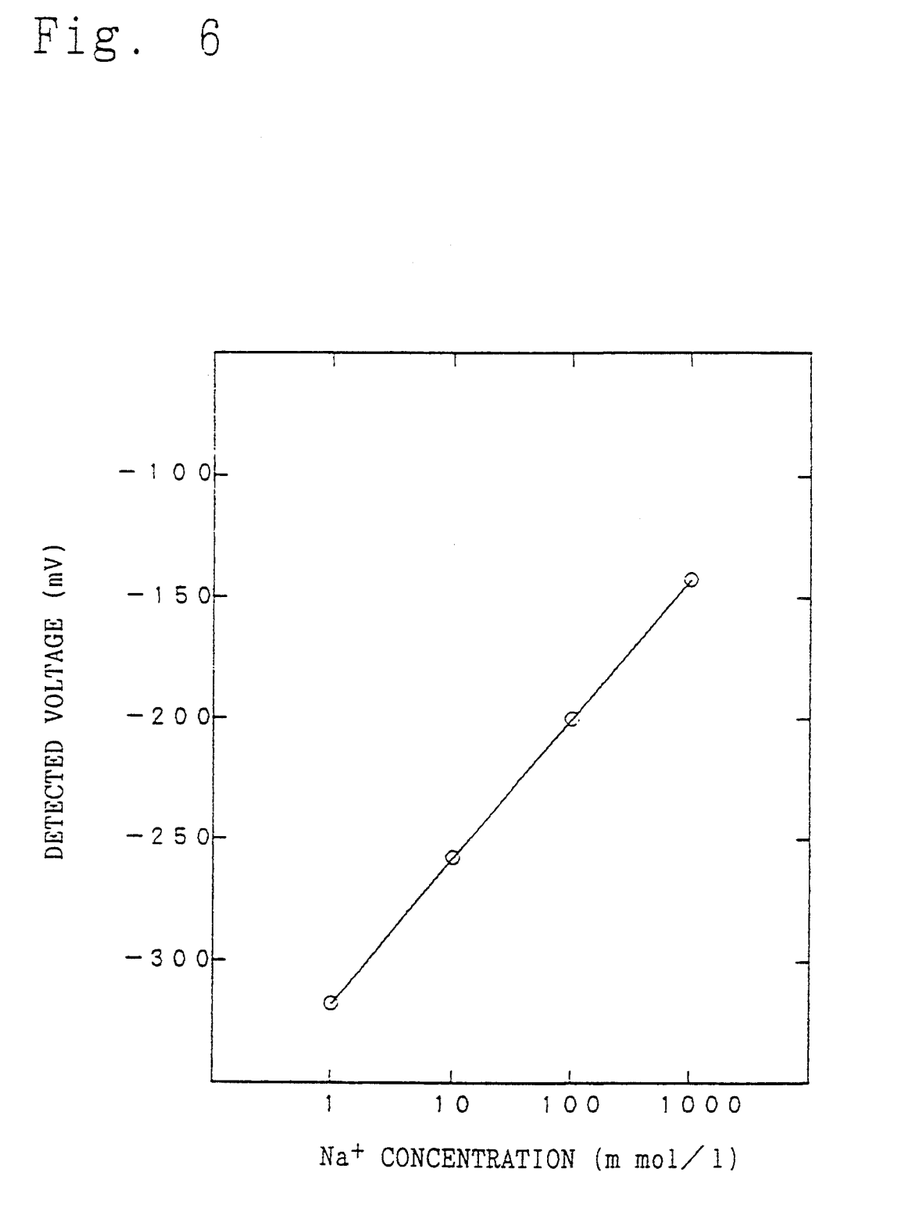
FIG. 6: A graph illustrating the variation in electric potential based on the ion concentration in a measuring test using an ion-selective electrode formed of an ionic bridge layer of Example 4.
Figure 7:
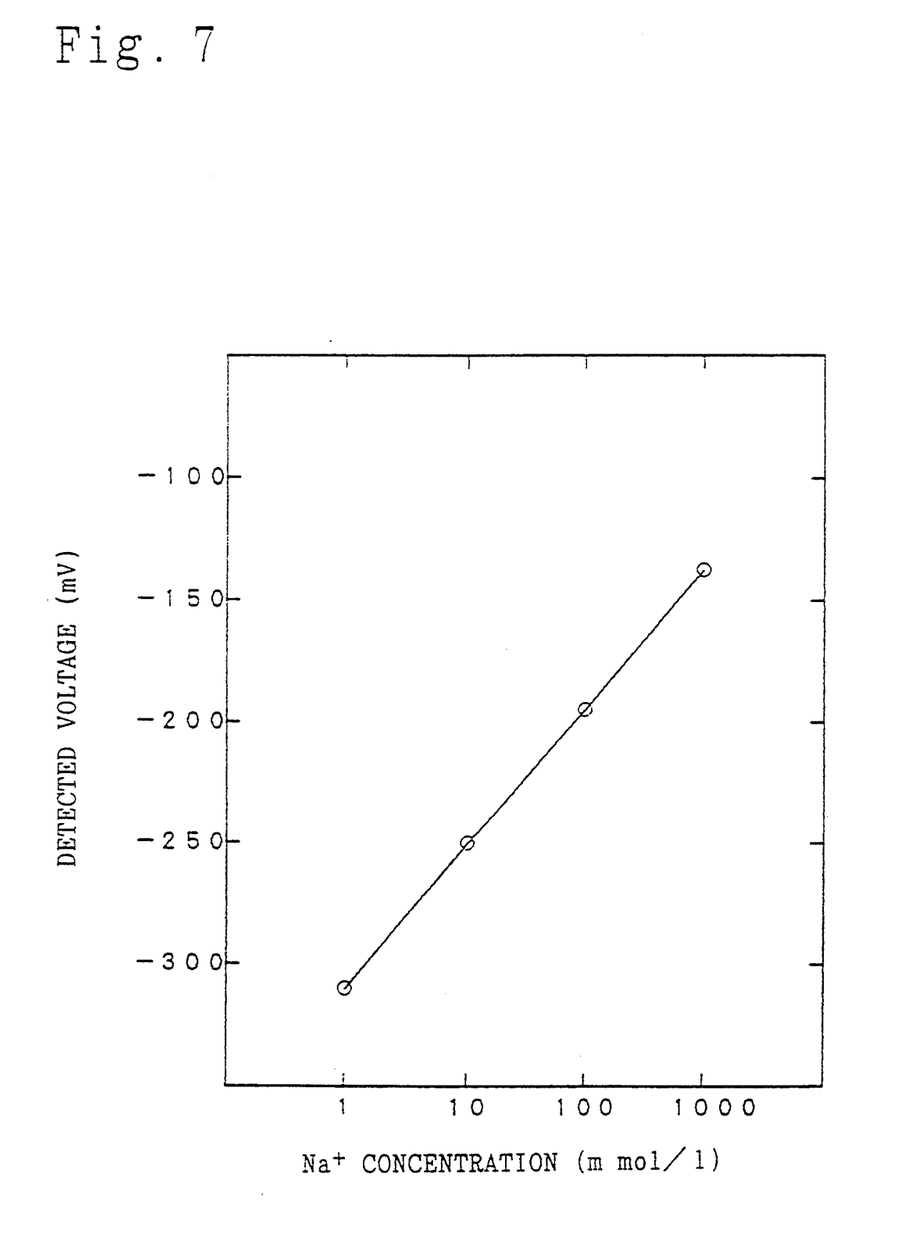
FIG. 7: A graph illustrating the variation in electric potential based on the ion concentration in a measuring test using an ion-selective electrode formed of the ionic bridge layer of Example 5.

The sodium-ion-selective electrodes of Examples 1 to 5 were used to perform potentiometry in such a manner as shown in FIG. 2 to obtain responses to the sodium ion, which are shown in FIGS. 3 to 7. As is clear from these figures, linear responses each following Nernst equation were obtained in a concentration range of 1 to 1000 m mol/l, showing the response time within a range of 30 seconds, and constant values for detected voltages (i.e., without fluctuation upon each measurement.).

As for Examples 1 to 8 and Comparative examples 1 to 3, five pieces of the ion-selective electrodes were prepared in each case, in which a sample solution having an $Na^+$ concentration of 50 m mol/l was measured in electric potential so that the fluctuations of the detected potentials or voltages were determined. The results are shown in Table 1. The ion-selective electrodes of the present invention are small in fluctuation of the detected voltage. Particularly, Example 3 was the smallest one with a maximum deviation of only 0.5 mV. In contrast with this, the comparative examples were poor in response, which made the performance of potentiometry impossible or show extremely wide fluctuation in the detected voltages.

TABLE 1

VOLTAGE VALUES (mV) DETECTED THROUGH ION-SELECTIVE ELECTRODES OF EXAMPLES 1 TO 5 IN MEASURING TEST

| ELECTRODE NO. | 1 | 2 | 3 | 4 | 5 | ([$Na^+$] = 50 mmol/l) MEAN | FLUCTUATION MAXIMUM DEVIATION IN mV |
|---|---|---|---|---|---|---|---|
| Ex. 1 | −72.6 | −97.1 | −90.7 | −79.8 | −84.3 | −84.9 | 25 |
| Ex. 2 | −135.6 | −137.6 | −139.0 | −138.5 | −137.3 | −137.6 | 3.5 |
| Ex. 3 | −151.7 | −151.4 | −151.6 | −151.8 | −151.9 | −151.7 | 0.5 |
| Ex. 4 | −207.0 | −222.9 | −218.4 | −229.3 | −212.1 | −217.9 | 24 |

TABLE 1-continued

VOLTAGE VALUES (mV) DETECTED THROUGH ION-SELECTIVE ELECTRODES
OF EXAMPLES 1 TO 5 IN MEASURING TEST

| ELECTRODE | | | | | | ([Na$^+$] = 50 mmol/l) | FLUCTUATION MAXIMUM |
| NO. | 1 | 2 | 3 | 4 | 5 | MEAN | DEVIATION IN mV |
| --- | --- | --- | --- | --- | --- | --- | --- |
| Ex. 5 | −217.7 | −207.4 | −206.7 | −211.4 | −213.8 | −211.4 | 11 |
| Ex. 6 | −136.2 | −137.5 | −136.5 | −137.1 | −137.4 | −136.9 | 1.3 |
| Ex. 7 | −77.0 | −69.3 | −73.8 | −70.3 | −75.6 | −73.2 | 7.7 |
| Ex. 8 | −148.9 | −148.5 | −148.1 | −149.2 | −148.4 | −148.6 | 1.1 |
| COMP. Ex. 1 | −128.3 | −200.8 | −169.7 | −290.3 | −183.9 | −194.6 | 162 |
| COMP. Ex. 2 | POOR RESPONSE | POOR RESPONSE | −152.0 | POOR RESPONSE | POOR RESPONSE | — | — |
| COMP. Ex. 3 | POOR RESPONSE | POOR RESPONSE | POOR RESPONSE | POOR RESPONSE | POOR RESPONSE | — | — |

IONIC BRIDGE LAYER: INTERNAL ELECTRODE
Ex. 1: AgCl + NaH$_2$PO$_4$.2H$_2$O/C.PASTE = 40 + 10/50 wt %: Cu
Ex. 2: AgCl + Na$_2$HPO$_4$/C.PASTE = 40 + 10/50 wt %: Cu
Ex. 3: AgCl + Na$_3$PO$_4$.12H$_2$O/C.PASTE = 40 + 10/50 wt %: Cu
Ex. 4: AgBr + Na$_3$PO$_4$.12H$_2$O/C.PASTE = 40 + 10/50 wt %: Cu
Ex. 5: AgI + Na$_3$PO$_4$.12H$_2$O/C.PASTE = 40 + 10/50 wt %: Cu
Ex. 6: AgCl + Na$_2$HPO$_4$/C.PASTE = 30 + 20/50 wt %: Cu
Ex. 7: AgCl + Na$_2$HPO$_4$/C.PASTE = 20 + 30/50 wt %: Cu
Ex. 8: AgCl + Na$_3$PO$_4$.12H$_2$O/C.PASTE = 40 + 10/50 wt %: Ag
COMP. Ex. 1: C.PASTE = 100 wt %: Cu
COMP. Ex. 2: AgCl + Na$_3$PO$_4$.12H$_2$O/C.PASTE = 20 + 5/75 wt %: Cu
COMP. Ex. 3: AgCl + Na$_2$HPO$_4$/C.PASTE = 10 + 40/50 wt %: Cu

Incidentally, in FIG. 2: the reference numeral 1 denotes an ion-selective electrode (which is constructed of an internal electrode 1a, ionic bridge layer 1b and an ion-sensitive membrane 1c); A denotes an ion-selective electrode; B a commercially available reference electrode; C a sample solution; 7 a recorder (which is constructed of an electrometer 7a and a pen recorder 7b); 8 a magnetic stirrer; and, 9 a stirring element.

It should be noted that modifications to any embodiment of the present invention obvious in the art may be done without departing from the gist and scope of the present invention as herein disclosed and as claimed hereinbelow.

What is claimed is:

1. In an ion-selective electrode comprising, in order from the measured-ion contact side: a solid electrolyte serving as an ion-sensitive membrane, an ionic bridge layer, and an internal electrode, the improvement wherein:
said ionic bridge layer is prepared by mixing a salt mixture with an electrically conductive resin composition at a salt mixture: resin ratio of 1:2 to 3:1 in weight, provided that the weight of said electrically conductive resin composition is determined after heat treatment thereof, and said salt mixture is prepared by mixing a silver halide with a sodium phosphate at a former:latter ratio of 9:1 to 3:7 in weight.

2. The ion-selective electrode as set forth in claim 1, wherein said ionic bridge layer is prepared by mixing said salt mixture with said electrically conductive resin composition at a composition:mixture ratio of 1:1 in weight, provided that the weight of said electrically conductive resin composition is determined after the heat treatment thereof.

3. The ion-selective electrode as set forth in claim 1, wherein said silver halide is selected from the group consisting of silver chloride, silver bromide and silver iodide.

4. The ion-selective electrode as set forth in claim 1, wherein said sodium phosphate is selected from the group consisting of sodium dihydrogen phosphate, disodium hydrogen phosphate, trisodium phosphate and hydrates thereof, and a mixture thereof.

5. The ion-selective electrode as set forth in claim 1, wherein said internal electrode is made of copper.

6. The ion-selective electrode as set forth in claim 1, wherein said salt mixture is prepared by mixing said silver halide with said sodium phosphate at a former:latter ratio of 9:1 to 7:3 in weight.

7. The ion-selective electrode as set forth in claim 6, wherein:
said salt mixture is prepared by mixing said silver halide with said sodium phosphate at a former:latter ratio of 8:2 in weight.

8. The ion-selective electrode as set forth in claim 1, wherein:
said electrically conductive resin composition of said ionic bridge layer essentially consists of a carbon-loaded adhesive resin composition.

9. The ion-selective electrode as set forth in claim 8, wherein said carbon has a grain size of the secondary order to be about 0.1 micrometer.

10. The ion-selective electrode as set forth in claim 1, wherein:
said solid electrolyte serving as said ion-sensitive membrane comprises a Na-ion conductive ceramic.

11. The ion-selective electrode as set forth in claim 10, wherein:
said Na-ion conductive ceramic is selected from the group consisting of Na-$\beta$-alumina, Na-$\beta''$-alumina and NASICON.

12. The ion-selective electrode as set forth in claim 1, wherein said silver halide is silver chloride.

13. The ion-selective electrode as set forth in claim 1, wherein said sodium phosphate is selected from the group consisting of sodium dihydrogen phosphate dihydrate, disodium hydrogen phosphate and trisodium phosphate 12-hydrate.

14. The ion-selective electrode as set forth in claim 1, wherein said electrically conductive resin composition comprises 10 to 60% in weight of a powdery electrically conductive material.

15. The ion-selective electrode as set forth in claim 1, wherein said resin composition has a good flowability in its initial stage and is cured to have a large adhesive strength.

16. The ion-selective electrode as set forth in claim 1, wherein said resin composition comprises a resin selected from the group consisting of unsaturated polyester resins, acrylic resins and polyurethane resins.

17. The ion-selective electrode as set forth in claim 1, wherein said salt is in a powdery state having a mean grain size of 50 micrometers or less.

18. The ion-selective electrode as set forth in claim 17, wherein said salt has a mean grain size of 10 micrometers or less.

19. The ion-selective electrode as set forth in claim 1, wherein said ion-selective electrode has a linear response curve of detected voltage at least at a concentration range of 1 to 1,000 m mol/l.

20. The ion-selective electrode as set forth in claim 19, wherein said ion-selective electrode has a response time within 30 seconds.

21. The ion-selective electrode as set forth in claim 1, wherein said electrically conductive resin composition forms an adhesive film after curing.

* * * * *